US009226653B2

(12) United States Patent
Torii et al.

(10) Patent No.: US 9,226,653 B2
(45) Date of Patent: Jan. 5, 2016

(54) METHOD FOR MONITORING IMAGE OF EXAMINEE'S EYE AND MONITORING SYSTEM

(75) Inventors: Hisanari Torii, Aichi (JP); Yukihiro Higuchi, Aichi (JP); Norimasa Satake, Aichi (JP)

(73) Assignee: NIDEK CO., LTD., Aichi (JP)

( * ) Notice: Subject to any disclaimer, the term of this patent is extended or adjusted under 35 U.S.C. 154(b) by 131 days.

(21) Appl. No.: 13/531,690

(22) Filed: Jun. 25, 2012

(65) Prior Publication Data
US 2012/0281184 A1 Nov. 8, 2012

(30) Foreign Application Priority Data

May 7, 2011 (JP) ................... 2011-103894

(51) Int. Cl.
*A61B 3/14* (2006.01)
*A61B 3/00* (2006.01)
(52) U.S. Cl.
CPC .................... *A61B 3/0025* (2013.01)
(58) Field of Classification Search
USPC ................. 351/200, 205, 206, 208, 221–222, 351/245–246
See application file for complete search history.

(56) References Cited

U.S. PATENT DOCUMENTS

| 7,510,282 B2 | 3/2009 | Ueno et al. |
| 2008/0024721 A1 | 1/2008 | Ueno et al. |
| 2010/0142781 A1* | 6/2010 | Walker et al. ................. 382/131 |
| 2010/0238403 A1* | 9/2010 | Kobayashi et al. ........... 351/206 |
| 2010/0277692 A1* | 11/2010 | Mukai et al. ................. 351/208 |

FOREIGN PATENT DOCUMENTS

| JP | 09-192106 | 7/1997 |
| JP | 2008029467 A | 2/2008 |

OTHER PUBLICATIONS

Kashiwagi, Hiroya., "My Electronic Medical Chart" IOL & RS vol. 19, No. 3, Sep. 2005, pp. 374-376; Partial English translation thereof.; Cited in Japanese Office Action.

* cited by examiner

*Primary Examiner* — Joseph P Martinez
*Assistant Examiner* — Brandi Thomas
(74) *Attorney, Agent, or Firm* — Rankin, Hill & Clark LLP

(57) ABSTRACT

A method for monitoring an image of an examinee's eye includes: obtaining first image data including a first examinee's eye image captured by a first ophthalmologic photographing apparatus, and additional information including type information on the first examinee's eye image; obtaining second image data including a second examinee's eye image captured by a second ophthalmologic photographing apparatus different from the first ophthalmologic photographing apparatus, and additional information including type information on the second examinee's eye image; recognizing the first examinee's eye image and the second examinee's eye image as the same type of images, based on the additional information; and correcting a difference between the first examinee's eye image and the second examinee's eye image.

18 Claims, 4 Drawing Sheets

METHOD FOR MONITORING IMAGE OF EXAMINEE'S EYE AND MONITORING SYSTEM

CROSS-REFERENCE TO RELATED APPLICATION

This application is based on Japanese Patent Application No. 2011-103894 filed with the Japan Patent Office on May 7, 2011, the entire content of which is hereby incorporated by reference.

BACKGROUND

1. Technical Field

The present invention relates to a method for monitoring an image of an examinee's eye, and a monitoring system.

2. Related Art

Ophthalmic photographing apparatuses include ophthalmic optical coherence (OCT) tomography apparatuses, fundus cameras, scanning laser ophthalmoscopes (SLOs), and the like. In a follow-up monitoring by an ophthalmic photographing system, there is a case where images of the same area are obtained at different inspection times and dates. For example, when an ophthalmic OCT apparatus is used, a tomographic image of the fundus is obtained multiple times. The course of a lesioned part is monitored based on the difference of the tomographic images.

In such monitoring, the following procedures are conceived. That is, image data corresponding to an obtained image is selected from an examinee's eye image stored in an ophthalmic image filing system. Then, by displaying this image data on a display monitor, the follow-up monitoring of the examinee's eye image is conducted.

Related technical literature: JP-A-2008-29467

SUMMARY

A method for monitoring an image of an examinee's eye includes: obtaining first image data including a first examinee's eye image captured by a first ophthalmologic photographing apparatus, and additional information including type information on the first examinee's eye image; obtaining second image data including a second examinee's eye image captured by a second ophthalmologic photographing apparatus different from the first ophthalmologic photographing apparatus, and additional information including type information on the second examinee's eye image; recognizing the first examinee's eye image and the second examinee's eye image as the same type of images, based on the additional information; and correcting a difference between the first examinee's eye image and the second examinee's eye image.

DETAILED DESCRIPTION

Figure 1:
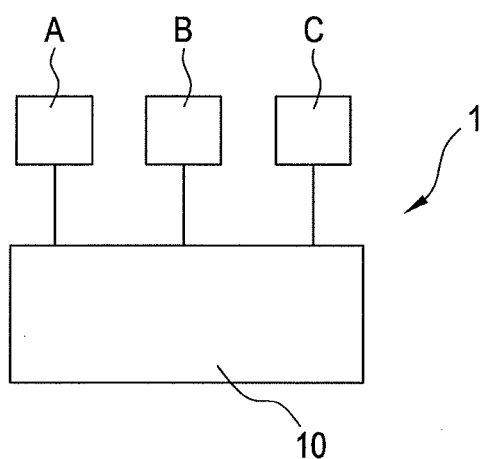
FIG. 1 is a diagram illustrating an example of an ophthalmic monitoring system according to one embodiment.

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

In the field of ophthalmology, the monitoring of an eye suffering from glaucoma is conducted for a several years. The period of the monitoring lasts several tens of years when it is long. After several years, the photographing method or the specification of photographing apparatuses may have been greatly changed. Also, even if a similar device is still used, it may be an upgraded version, or an alternative successor. In such a case, the functions of the photographing apparatus or a certain means for obtaining an image may have been changed.

Therefore, when a new product of the same manufacturer or a product of a different manufacturer is used as a new monitoring device (when it is substituted for a conventional device, or used in combination with the conventional device), it is difficult to correlate the new device with the conventional device. Therefore, there is a possibility that the long-term monitoring cannot be effectively and appropriately conducted.

An object herein is to provide a method for monitoring an image of an examinee's eye image, which is adaptable to a long-term monitoring.

A method for monitoring an image of an examinee's eye includes: obtaining first image data including a first examinee's eye image captured by a first ophthalmologic photographing apparatus, and additional information including type information on the first examinee's eye image; obtaining second image data including a second examinee's eye image captured by a second ophthalmologic photographing apparatus different from the first ophthalmologic photographing apparatus, and additional information including type information on the second examinee's eye image; recognizing the first examinee's eye image and the second examinee's eye image as the same type of images, based on the additional information; and correcting a difference between the first examinee's eye image and the second examinee's eye image.

This method is adaptable to a long-term monitoring.

Embodiments disclosed herein will be described below with reference to the accompanying drawings.

FIG. 1 is a diagram illustrating an example of an ophthalmic monitoring system according to an embodiment. An ophthalmic monitoring system 1 monitors an examinee's eye by arithmetically processing a plurality of tomographic images obtained at different times and dates. The ophthalmic monitoring system 1 has, for example, an image processing apparatus 10, a first ophthalmic photographing apparatus A (photographing apparatus A), a second ophthalmic photographing apparatus B (photographing apparatus B), and a third ophthalmic photographing apparatus C (photographing apparatus C).

These photographing apparatuses are connected via a network (bus, LAN or the like). Therefore, the photographing apparatuses are capable of mutually transmitting and receiving image data and the like. Note that the ophthalmic monitoring system 1 may not simultaneously have the photographing apparatus A, the photographing apparatus B, and the photographing apparatus C. The ophthalmic monitoring system 1 is adaptable to a case where one photographing apparatus is replaced with another photographing apparatus in long term monitoring.

The photographing apparatus A, the photographing apparatus B, and the photographing apparatus C each include an OCT device having a tomographic photographing optical system (e.g., Optical Coherence Tomography: OCT). In the OCT device of the photographing apparatuses A to C, light flux emitted from a light source is divided into measurement light and reference light. The measurement light flux is guided to the fundus of the examinee's eye. On the other hand, the reference light is guided to a reference optical system. An interference status between the measurement light reflected at the fundus and the reference light is detected by a detector. Then, by image processing of received light signals output from the detector, a tomographic image is obtained.

In this embodiment, the photographing apparatuses A, B and C each have different front imaging optical systems. That is, the photographing apparatuses A, B and C obtain similar tomographic images. In addition, the photographing apparatuses A, B and C also each obtain fundus front images of different types.

For example, the photographing apparatus A includes a so-called Scanning Laser Ophthalmoscope: SLO. That is, the photographing apparatus A includes an optical scanner and a light receiving element. The optical scanner two-dimensionally scans a fundus by measurement light (e.g., infrared light) emitted from a light source. The light receiving element receives light reflected from the fundus through a confocal opening provided at a substantially conjugated position with respect to the fundus. Then, a fundus front image (SLO front image) is obtained based on received light signals output from the light receiving element. The scanning region regarding the OCT and the scanning region to obtain an SLO image are set in advance to be identical. In this manner, a tomographic image corresponding to each position of the SLO front image is obtained by the OCT. As a result, the fundus front image and the tomographic image are correlated with each other.

The photographing apparatus B obtains a fundus front image based on the interference signals of the OCT, using the OCT front image photographing optical system to obtain the fundus front image. For example, the photographing apparatus B two-dimensionally scans measurement light, and integrates the spectrum intensity of interference signals from the light receiving element with respect to each point on an XY plane. In this manner, an OCT front image is obtained. A fundus front image is obtained based on a tomographic image. Therefore, a tomographic image corresponding to each position of an OCT front image is obtained by the OCT. As a result, the OCT front image and the tomographic image are correlated with each other.

The photographing apparatus C has a fundus camera optical system for photographing the fundus of an examinee's eye. The photographing apparatus C obtains a camera front image (e.g., a color fundus image or an infrared fundus image). The camera front image is obtained by photographing the fundus by the fundus camera. The scanning region of the OCT and a pixel region of the fundus camera are set in advance to be identical. In this manner, a tomographic image corresponding to each pixel position of the camera front image is obtained by the OCT. As a result, the camera front image and the tomographic image are correlated with each other.

The image processing apparatus 10 obtains, for example, image data captured by the photographing apparatuses A to C (including data of a tomographic image and a front image) through a network. The image processing apparatus 10 stores and manages the image data together with additional information provided thereto. Here, the additional information may be information about the apparatus and information about type of the image to be processed in the apparatus (e.g., the image type may be tomographic or front). For instance, the image processing apparatus 10 recognizes front images obtained by different image obtaining methods in apparatuses A to C as the same type of images. That is, the image processing apparatus 10 handles the image data of these images as uniform image data. The image processing apparatus 10 analyzes the images and displays the analysis result along with the images (described in further detail below).

The photographing apparatuses A to C each transmit obtained image data and additional data to the image processing apparatus 10 through a network, either automatically or upon an instruction by an examiner (manually).

Figure 2:
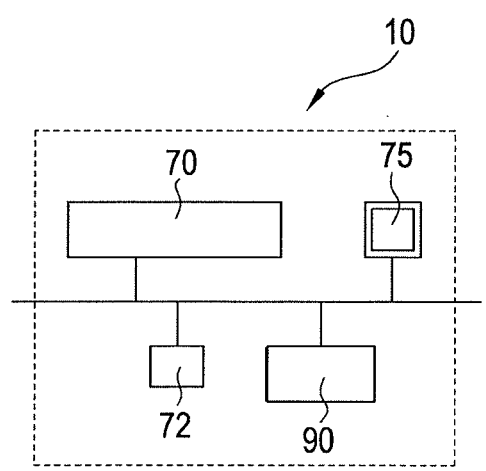
FIG. 2 is a block diagram illustrating a configuration of an image processing apparatus.

FIG. 2 is a block diagram showing a configuration of the image processing apparatus 10.

As shown in FIG. 2, the image processing apparatus 10 has a data management unit 70, an operation unit 90, a data display unit (monitor or the like) 75, and a data storage unit (memory) 72.

The operation unit 90 is a unit to be operated by an examiner. The operation unit 90 has different switches, a mouse, and the like for receiving various instructions from the examiner.

The monitor 75 displays images and results obtained by analyzing such images under the control of the data management unit 70.

The data management unit 70 collectively controls the operations of the data management unit 70, the monitor 75, and the memory 72 to manage image data obtained by the photographing apparatuses A to C.

The data management unit 70 handles front images (SLO front image, OCT front image, and camera front image) obtained by the photographing apparatuses A to C as front images of the same examinee, using additional information added to them. The images of the image data obtained by the photographing apparatuses A to C are classified into tomographic images and front images based on the additional information. These image data is stored in the memory 72 as uniform image data (the details will be described later).

Hereafter, image data (including a tomographic image and a front image) obtained by one of the photographing apparatuses A to C (the first photographing apparatus) is referred to as the first image data. A fontal image included in the first image data is referred to as the first front image (the first examinee's eye image), whereas a tomographic image is referred to as the first tomographic image (the first examinee's eye image).

In addition, image data (including a tomographic image and a front image) obtained by another one of the photographing apparatuses A to C (the second photographing apparatus) is referred to as the second image data. A fontal image included in the second image data is referred to as the second front image (the second examinee's eye image), whereas a tomographic image is referred to as the second tomographic image (the second examinee's eye image).

The data management unit 70 has an image analysis function. The data management unit 70 arithmetically processes the first and second image data stored in the memory 72. In other words, the image data is classified into the first and second data and analyzed based on the additional information (hereinafter referred to as image data). From the result of the image analysis, for example, the data management unit 70 calculates an abnormal area in each location on the fundus. In addition, the data management unit 70 creates, for example, a map that two-dimensionally represents the abnormal area of each location on the fundus (hereinafter referred to as analysis map).

The memory 72 stores additional information for classifying image data, and various control programs for controlling the operation of each unit and the like. The memory 72 stores image data, such as front images and tomographic images correlated therewith. Such kinds of the image data have been obtained by the photographing apparatuses A to C, together with additional information added to each image (image data).

For example, the first photographing apparatus (for example, the photographing apparatus A) captures the first front image (SLO front image) of the examinee's eye, using the first photographing mode (SLO). In addition, the first photographing apparatus obtains a tomographic image of the examinee's eye, using an optical interferometry technique. This tomographic image is correlated with the first front image. That is, the first photographing apparatus obtains the first image data including a tomographic image and a first front image. The first image data is stored in the memory 72, together with additional information added to the images included therein.

Furthermore, the second photographing apparatus (for example, the photographing apparatus B) captures the second front image (OCT front image) of the examinee's eye, using the second photographing mode (OCT) different from the first photographing mode. In addition, the second photographing apparatus obtains a tomographic image of the examinee's eye, using an optical interferometry technique. This tomographic image is correlated with the second front image. That is, the second photographing apparatus obtains the second image data including a tomographic image and a second front image. The second image data is stored in the memory 72, together with additional information added to the images included therein.

Figure 3:
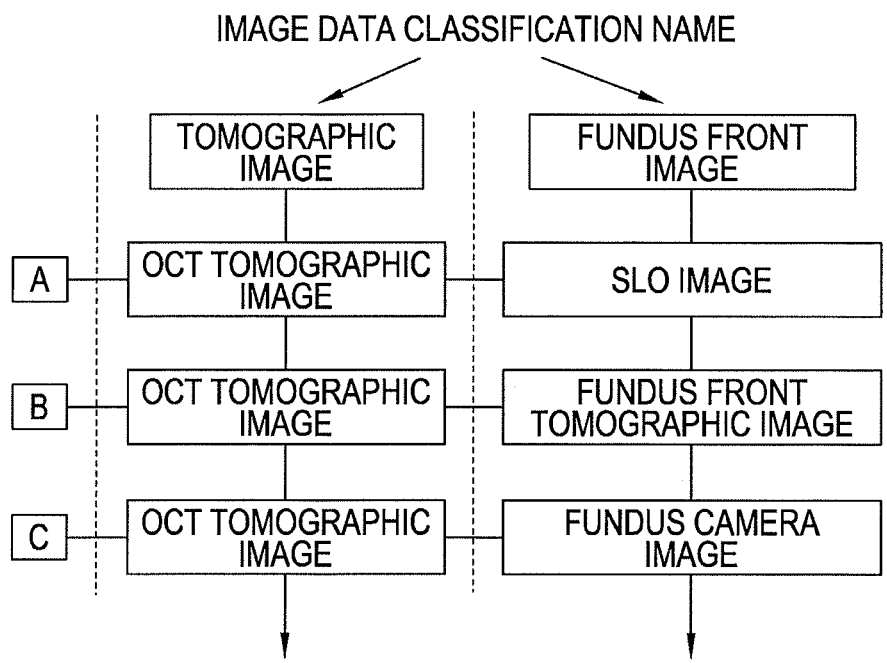
FIG. 3 is a diagram illustrating the concept of a management function (image data management function) for device information and image type information included in additional information.

Here, the management of device information and image type information using additional information will be described. FIG. 3 is a diagram showing the concept of a management function (image data management function) for device information and image type information included in additional information. FIG. 3 shows types of devices on the vertical axis. The horizontal axis shows types of images obtained by each device.

For example, in the photographing apparatus A, image data obtained as a tomographic image is handled as tomographic data. In addition, in the photographing apparatuses B and C, image data obtained as a tomographic image is handled similarly.

On the other hand, in the photographing apparatus A, the image data of an SLO front image obtained by the SLO is handled as image data as "fundus front image". In addition, in the photographing apparatus B, the image data of an OCT front image obtained by the OCT is handled as the same type of (or common) image data as "fundus front image," as with the SLO front image. In the photographing apparatus C, the image data of a camera front image obtained by the fundus camera is handled as the same image data as "fundus front image," as with other front images. That is, the fundus front images obtained by different modes by the photographing apparatuses A to C are handled as the same type of (or uniform) image data.

The memory 75 stores classification information (e.g., data table) for classifying images based on additional information added to each image (see FIG. 3). For example, regarding the classification processing of images, the memory 75 stores information that, regarding the photographing apparatus A, an OCT tomographic image obtained by the photographing apparatus A is classified as a tomographic image, and an SLO image is classified as a fundus front image. That is, the memory 75 stores information that, regarding the photographing apparatus A, an OCT image is handled as a tomographic image while an SLO image is handled as a fundus front image.

The data management unit 70 classifies the image data obtained by the photographing apparatuses A to C with reference to the classification information. That is, the data management unit 70 refers to the classification information stored in the memory 75 to classify the image data. Then, the data management unit 70 classifies the image data obtained by the photographing apparatuses A to C, using the additional information.

An update of the classification information is conducted by, for example, inputting the classification information on a new photographing apparatus into the data management unit 70 by the examiner. Once the examiner inputs the classification information on the new photographing apparatus, the data management unit 70 transmits the input classification information to the memory 75. The memory 75 stores this classification information.

Figure 4:
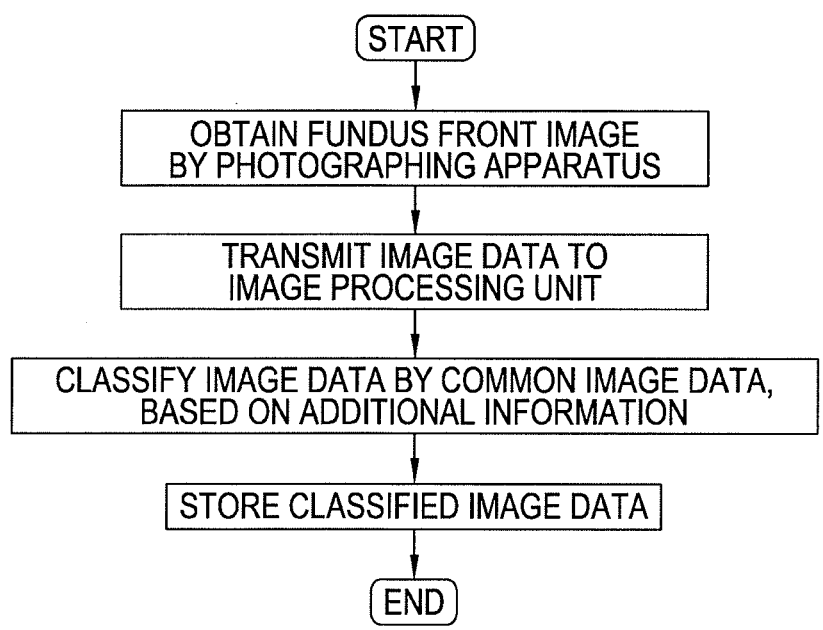
FIG. 4 is a flowchart illustrating the control operations of a data management unit.

FIG. 4 is a flowchart showing the control operations of the data management unit 70. Hereafter, the management operations for classifying image data by the data management unit 70 will be described in further details, with reference to the flowchart.

In the example shown below, it is assumed that a fundus was captured by the photographing apparatus A and its fundus front image was obtained in the past. It is further assumed that then a monitoring of the fundus is conducted using another photographing apparatus B.

Firstly, a description will be made regarding the handling of image data obtained by the photographing apparatus A, which serves as a reference for a follow-up monitoring.

The image data including an SLO front image and a fundus tomographic image obtained by the photographing apparatus A is automatically transmitted to the image processing apparatus 10. The transmitted image data is attached with additional information for classifying the image data. For example, the SLO image is provided with additional information indicating that it is a fundus front image (e.g., image type information).

After the image data of the SLO front image obtained by the photographing apparatus A is transmitted to the image processing apparatus 10, the data management unit 70 classifies the SLO image as a fundus front image, using the additional information of the image data stored in the memory 72.

That is, the data management unit 70 refers to the classification information stored in the memory 72 as described above. Then, the data management unit 70 classifies the image data of the SLO image as image data of a common fundus front image. Then, the image data of the SLO image is stored in the memory 72 as image data of a fundus front image.

A description is now made of the handling of an image obtained by the photographing apparatus B. Follow-up monitoring is conducted using this image and an image obtained by the photographing apparatus A.

After image data including an OCT front image is obtained by the photographing apparatus B, this image data is automatically transmitted to the image processing apparatus 10. The transmitted image data is attached with additional information for classifying this image data. For example, the OCT image is provided with additional information indicating that it is a fundus front image (e.g., image type information).

After the image data of the OCT front image obtained by the photographing apparatus B is transmitted to the image processing apparatus 10, the data management unit 70 classifies the OCT front image as a fundus front image, using the additional information of image data stored in the memory 72. That is, the data management unit 70 refers to the classification information stored in the memory 72. Then, the data management unit 70 stores in the memory 72 the image data of the OCT front image as image data of a fundus front image.

The camera front image obtained by the photographing apparatus C is also stored in the memory 72 as image data of a fundus front image.

As described above, the data management unit 70 recognizes (handles) a plurality of fundus front images obtained by different photographing apparatuses as the same type of (or common) image data.

Subsequently, the data management unit 70 analyzes the image data of the fundus front image stored in the memory 72. For example, the data management unit 70 analyzes the image data obtained by the photographing apparatus A, and the image data obtained by the photographing apparatus B. The data management unit 70 reads from the memory 72 the image data of the fundus front image obtained by the photographing apparatuses A and B, and analyzes it.

Here, the data management unit 70 detects information concerning a displacement (difference) between the fundus front image obtained by the photographing apparatus A (the first front image) and the fundus front image obtained by the photographing apparatus B (the second front image). The data management unit 70 compares and analyzes two tomographic images of different examination times and dates, based on the detected displacement information. These tomographic images are namely the fundus tomographic image obtained by the photographing apparatus A (the first tomographic image), and the fundus tomographic image obtained by the photographing apparatus B (the second tomographic image).

The data management unit 70 creates, for example, a map two-dimensionally showing the layer thickness of the fundus in accordance with each tomographic image (hereinafter referred to as layer thickness map), based on the analysis result of two tomographic images. As described above, the fundus tomographic image and the fundus front image are correlated with each other. Therefore, it allows the fundus front image and the layer thickness map to be associated with each other. The data management unit 70 compares the image data of the fundus front image obtained by the photographing apparatuses A and B. The data management unit 70 references to this comparison result to compare two layer thickness maps.

The mapped (graphed) information of the fundus layer thickness may be information concerning the thickness of the layer of the fundus in the depth direction (Z direction). This information may be, for example, the thickness of each layer, or the total thickness of a plurality of layers. These layers include, for example, the thickness of the nerve fiber layer, and the thickness from the retinal surface to the choroid.

Hereinafter, the analysis will be specifically described.

Figure 5:
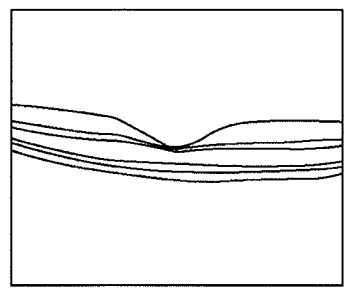
FIG. 5 is a diagram illustrating an exemplary tomographic image obtained by an OCT.

FIG. 5 is a diagram illustrating an example of a tomographic image obtained by an OCT. The data management unit 70 detects the layer information of the fundus in obtained fundus front image by image processing. The detection result is stored in the memory 72 together with the image data.

In the case of detecting a layer, for example, the brightness level of a tomographic image is detected. After that, the boundary of the layer corresponding to a certain retinal layer (e.g., the retinal surface and the pigment epithelial layer) is extracted by image processing. Then, the layer thickness is measured by measuring a space between the boundaries.

Figure 6:
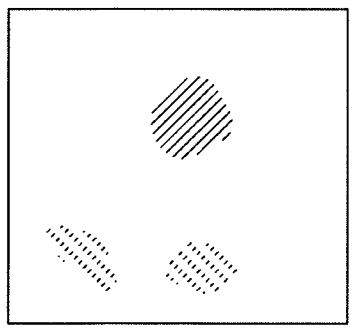
FIG. 6 is a diagram illustrating an exemplary two-dimensional map representing a layer thickness based on the position of the fundus.

Then, the data management unit 70 calculates the thickness of the layer of the retina (e.g., the retinal surface and the pigment epithelial layer) based on the tomographic image. FIG. 6 is a diagram illustrating an analysis result of a tomographic image. This figure shows a map (a layer thickness map) two-dimensionally showing a layer thickness depending on a position of a fundus as an example. In this embodiment, the data management unit 70 creates a layer thickness map based on the obtained analysis result. In this layer thickness map, the analysis result of the tomographic image is shown in graphic. The layer thickness map shows, for example, two-dimensional distribution data regarding the layer thickness of the fundus.

In the layer thickness map, the layer thickness is indicated in color-coding. For example, the region having a layer thickness of 450 μm is indicated in red (oblique solid line in FIG. 6), the region having a layer thickness of 300 μm is indicated in green, and the region having a layer thickness of 200 μm is indicated in blue (oblique dotted line in FIG. 6). The data management unit 70 creates a layer thickness map regarding a plurality of tomographic images obtained by a plurality of photographing apparatuses. The data management unit 70 stores the layer thickness map in the memory 72.

Subsequently, the data management unit 70 creates a differential map showing a comparison result between layer thickness maps. Of course, the data management unit 70 may transmit the data of a layer thickness map of each device to the monitor 75 to display the data, without creating the differential map.

Figure 7A:
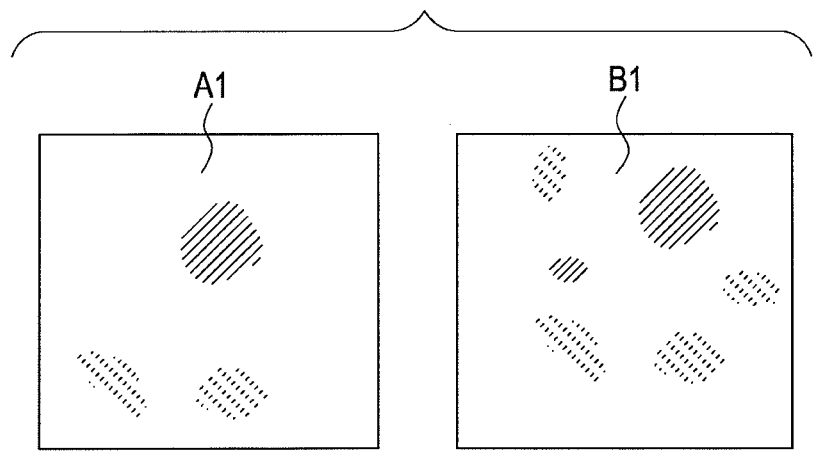
FIGS. 7A to 7C are diagrams each illustrating an exemplary differential map.
Figure 7B:
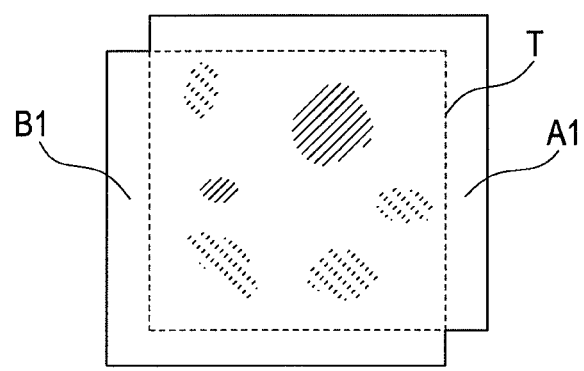
Figure 7C:
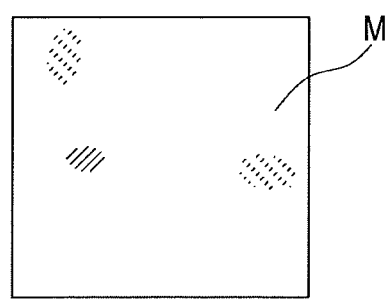

FIGS. 7A to 7C are diagrams illustrating an example of a differential map. The differential map will be now described with reference to FIGS. 7A to 7C. For example, as shown in FIG. 7A, a difference between a layer thickness map A1 concerning a tomographic image obtained by the photographing apparatus A and a layer thickness map B1 concerning a tomographic image obtained by the photographing apparatus B is detected. At this time, two fundus front images obtained by the photographing apparatuses A and B are used to detect a differential of common fundus regions. That is, the data management unit 70 matches the positions of these images as much as possible.

For example, the data management unit 70 detects a displacement between fundus front images. The data management unit 70 extracts the features of two fundus front images (e.g., mammilla, macula, or blood vessel). Then, the direction of the displacement and the amount of the displacement between the features are detected. The data management unit 70 adjusts the relative positions of two fundus front images based on the detection result. On the other hand, there is a correlation between a layer thickness map and a fundus front image. Therefore, by the above-mentioned positioning adjustment, the layer thickness map A1 and the layer thickness map B1 can be aligned (see FIG. 7B). Of course, the method for aligning the layer thickness maps is not limited to the technique of adjusting the relative position between the fundus front images. The alignment of the layer thickness maps may be done in accordance with the detection result of the displacement.

Upon the completion of the alignment of the layer thickness maps, the data management unit 70 obtains differential data by calculating the differential between the layer thickness maps. Then, based on the differential data, the data management unit 70 creates a differential map M of a common region T within two fundus tomographic images obtained by the photographing apparatuses A and B (see FIG. 7C).

As shown in FIG. 7C, in the differential map M, regions where differences in layer thickness have been detected within two fundus tomographic images are indicated with colors. For example, a region that is thicker on the layer thickness map B1 than on the layer thickness map A1 is indicated in red (oblique solid line in FIG. 7C). A region having a uniform layer thickness is indicated in green. Furthermore, a region that is thicker on the layer thickness map A1 than on the layer thickness map B1 is indicated in blue (oblique dotted line in FIG. 7C). That is, the color of the regions changes in accordance with the change in the layer thickness in the fundus. In this manner, the changes of the layer thickness of the fundus between the tomographic image obtained by the photographing apparatus A and the tomographic image obtained by the photographing apparatus B can be monitored.

As described above, in this embodiment, the mode for obtaining a fundus front image is different between the photographing apparatuses A and B. Even in such a case, a differential map corresponding to the fundus front images can be obtained. Then, according to the differential map, the tomographic images obtained by different photographing apparatuses can be adequately compared. In this manner, even in the case where several years have passed since the previous monitoring and the measurement principle or the specification of the photographing apparatus has been largely changed, the change of the fundus can be adequately detected. That is, an adequate follow-up monitoring can be conducted.

The data of a front image may be used for adjusting scanning positions in different photographing apparatuses. For example, the photographing apparatus B obtains, from the memory (database), scanning position information corresponding to an SLO image and a tomographic image (the first tomographic image) obtained by the photographing apparatus A. Then, the photographing apparatus B detects a displacement between an OCT front image obtained by itself and the SLO image by image processing. Then, the photographing apparatus B controls an optical scanner so as to correct the scanning position information obtained by the memory, with the detected displacement. In this manner, the alignment for the same area is done.

The mode of detecting a displacement between two images is not limited to a mode of extracting common features and detecting the direction of displacement and the amount of displacement of the extracted features. For example, as a mode of detecting a displacement between two images, it is possible to use various modes of image processing (a method using various types of correlation functions, a method using a Fourier transformation, and a method detecting the displacement of the peak positions of brightness distribution in the depth direction).

In this embodiment, a layer thickness map is detected for a follow-up monitoring. However, the present invention is not limited to this, and the following mode is possible, for example. That is, it may measure a layer thickness corresponding to each position, and determine whether the measuring result is within a certain range in the normal eye database (for example, a normal range corresponding to the measuring value of a normal eye). In this method, for example, a thickness determination, shape determination, and size determination of a certain area (for example, mammilla and macula) for each layer are conducted. Then, for example, whether the fundus is normal or not is determined. Furthermore, two-dimensional distribution data regarding the normal/abnormal area of a fundus may be detected.

There may be a case where the scale of an obtained front image is different depending on a photographing apparatus. In this case, a difference between the scale of the first front image and the scale of the second front image is included in a point of difference of both images. The data management unit 70 may make the scales of the first front image and the second front image substantially the same by enlarging or downsizing at least one of the first front image and the second front image. In addition, the data management unit 70 may adjust the scale of each front image to be a certain scale. Furthermore, the data management unit 70 may adjust the scale of one of the front images to match the scale of the other front image.

According to this embodiment, while the photographing apparatuses A to C of the ophthalmic monitoring system 1 have the same type of members for obtaining a tomographic image, they have different members for obtaining a fundus front image. However, the present invention is not limited to this, and the photographing apparatus of the ophthalmology monitoring system 1 only needs to have a member for obtaining the same type of (or common) images. Besides the spectrum domain OCT using a spectrometer, which is used in this embodiment, the member for obtaining the same type of images may be, for example, a Swept-Source OCT (SS-OCT) having a wave length variable light source, and a Time-Domain OCT (TD-OCT).

In addition, there may be a case where the scale of an obtained tomographic image varies depending on a photographing apparatus. In this case, the first photographing apparatus obtains the first image data including the first tomographic image, using an optical interferometry technique. Then, the second photographing apparatus obtains the second image data including the second tomographic image at a different photographic scale, using an optical interferometry technique. These image data are stored in the memory 72 together with additional information.

The data management unit 70 may match the scales of the first tomographic image and the second tomographic image in the depth direction and lateral direction by enlarging or downscaling at least one of the first tomographic image and the second tomographic image. In this case, the data management unit 70 may adjust the scale of each tomographic image to be a certain scale. In addition, the data management unit 70 may adjust the scale of one of the tomographic images to match the scale of the other tomographic image.

In this case, for example, the scales of the first tomographic image and the second tomographic image are adjusted to be the same, using the actual dimension data of the tomographic image per pixel (the depth direction and the lateral direction). Furthermore, when the tomographic image is three-dimensional data, the scale is adjusted in the depth direction and also adjusted in the X-Y two-dimensional direction, which is perpendicular to the depth direction.

In this embodiment, fundus photographing apparatuses for capturing fundus front images and fundus tomographic images are exemplified. However, the ophthalmology photographic system according to this embodiment is not limited to these. The technique of this embodiment may be applied to an anterior segment photographic system. The anterior segment photographic system captures an anterior segment front image and an anterior segment tomographic image. In this case, the anterior segment photographic system may have three different photographing apparatuses as in the structure shown in FIG. 1. That is, the first photographing apparatus has an SLO. In this photographing apparatus, the anterior segment of an examinee's eye is scanned by laser beam. An anterior segment front image is obtained by receiving reflected light from the anterior segment through a confocal opening. In addition, the second photographing apparatus has an OCT front image photographing optical system. In the second photographing apparatus, the examinee's eye anterior segment is scanned by the OCT measurement light. An anterior segment front image is obtained by receiving synthetic light of reflected light and reference light from the anterior segment. In addition, the third photographing apparatus has a fundus camera optical system. In the third photographing apparatus, the examinee's eye anterior segment is integrally irradiated with illumination light. An anterior segment front image is obtained by receiving reflected light from the anterior segment at a two-dimensional photographing element.

In addition, the photographing apparatuses A to C shown in FIG. 1 may be set so as to obtain a tomographic moving image, a two-dimensional moving image, and a three-dimensional moving image. Furthermore, the monitor 75 may be capable of displaying image data on which an analysis has been done. The monitor 75 may display an image classified from additional information added to each image datum by the data management unit 70. In addition, the first photographing mode or the second photographing mode may be modes using any one of the SLO, the OCT front image photographic optical systems, the fundus camera optical system and the like in the photographing apparatuses shown in FIG. 1.

In addition, the method disclosed herein may be any of the following first to tenth methods. That is, the first method is a method for follow-up monitoring an examinee's eye image obtained by an ophthalmologic photographing apparatus. This method includes: obtaining first data including an examinee's eye image captured by the first ophthalmologic photographing apparatus having an optical system for obtaining the examinee's eye image; obtaining second image data including an examinee's eye image captured by the second ophthalmologic photographing apparatus having an optical system for obtaining the examinee's eye image having a configuration different from the first ophthalmologic photographing apparatus; storing in a memory unit the first image data and the second image data together with additional information added to each image; integrating the first image data and the second image data based on additional information; and correcting a displacement between the first image data and the second image data, the displacement being produced by an individual difference between the first ophthalmologic photographing apparatus and the second ophthalmologic photographing apparatus.

The second method is the method according to the first method, including aligning the examinee's eye image of the first image data and the examinee's eye image of the second image data, which have been integrated.

The third method is the method according to the first method, including changing the scale of at least any one of the examinee's eye image of the first image data and the examinee's eye image of the second image data to match the scales of the examinee's eye images of the first image data and the second image data, which have been integrated.

The fourth method is the method according to the first method, where the first ophthalmologic photographing apparatus has a first photographing optical system for obtaining a first front image, the first image data includes at least the first front image captured by the first photographing optical system, the second ophthalmologic photographing apparatus has the second photographing optical system for obtaining a second front image having a configuration different from the first ophthalmologic photographing apparatus, and the second image data includes at least the first front image captured by the second photographing optical system.

The fifth method is the method according to the fourth method, where the first ophthalmologic photographing apparatus further has a first interferometry optical system for obtaining a first tomographic image, the first image data further includes at least the first tomographic image captured by the first interferometry optical system, the second ophthalmologic photographing apparatus further includes a second interferometry optical system for obtaining a second tomographic image having a configuration different from the first ophthalmologic photographing apparatus, the second image data further including at least the second tomographic image captured by the second interferometry optical system, displacement information between the first front image of the first image data and the second front image of the second image data, which have been integrated, is obtained, and the displacement between the first tomographic image of the first image data and the second tomographic image of the second image data, which have been integrated, is corrected based on the obtained displacement information.

The sixth method is the method according to the first method, where the first ophthalmologic photographing apparatus has a first interferometry optical system for obtaining a first tomographic image, the first image data includes at least the first tomographic image captured by the first interferometry optical system, the second ophthalmologic photographing apparatus has a second interferometry optical system for obtaining the second tomographic image having a configuration different from the first ophthalmologic photographing apparatus, and the second image data includes at least the second tomographic image captured by the second photographing optical system.

The seventh method is the method according to the sixth method, including: analyzing each of the first tomographic image of the first image data and the second tomographic image of the second image data, which have been integrated, by image processing; and obtaining differential data between the analysis result of the first tomographic image and the analysis result of the second tomographic image.

The eighth method is the method according to the seventh method, including displaying on a monitor a difference map made based on the obtained differential data.

The ninth method is the method according to the sixth method, where the first tomographic image and the second tomographic image are fundus tomographic images, each of the first tomographic image and the second tomographic image, which have been integrated, is analyzed by image processing, to obtain layer thickness information of the fundus, and differential data between the layer thickness information of the fundus based on the first tomographic image and the layer thickness information of the fundus based on the second tomographic image is obtained.

The tenth method is the method according to the sixth method, where, when the size of the photographing regions is different between the first tomographic image and the second tomographic image, with respect to a photographing region common between the first tomographic image and the second tomographic image, differential data between an analysis result based on the first tomographic image and an analysis result based on the second tomographic image is obtained.

These methods are adaptable to a long term monitoring.

The foregoing detailed description has been presented for the purposes of illustration and description. Many modifications and variations are possible in light of the above teaching. It is not intended to be exhaustive or to limit the examinee matter described herein to the precise form disclosed. Although the examinee matter has been described in language specific to structural features and/or methodological acts, it is to be understood that the examinee matter defined in the appended claims is not necessarily limited to the specific features or acts described above. Rather, the specific features and acts described above are disclosed as example forms of implementing the claims appended hereto.

What is claimed is:

1. A method for monitoring an image of an examinee's eye, comprising:
    obtaining first image data including a first examinee's eye image captured by a first ophthalmologic photographing apparatus, and additional information for determining whether the first examinee's eye image is a tomographic image or a front image;
    obtaining second image data including a second examinee's eye image captured by a second ophthalmologic photographing apparatus different from the first ophthalmologic photographing apparatus, and additional information regarding whether the second examinee's eye image is a tomographic image or a front image;
    determining whether the first examinee's eye image and the second examinee's eye image are a tomographic image or a front image, based on the additional information; and
    when the first examinee's eye image and the second examinee's eye image are a tomographic image or the first examinee's eye image and the second examinee's eye image are a front image, correcting a difference between the first examinee's eye image and the second examinee's eye image; and
    comparing the first examinee's eye image with the second examinee's eye image after the difference is corrected, wherein
    the first examinee's eye image is captured on a day that is different from a day on which the second examinee's eye image is captured; and
    the first ophthalmologic photographing apparatus comprises a first tomographic photographing optical system and a first front imaging optical system, and the second ophthalmologic photographing apparatus comprises a second tomographic photographing optical system and a second front imaging optical system, wherein a photographing method of the first tomographic photographing optical system and a photographing method of the second tomographic photographing optical system are different from each other;
    a photographing method of the first front imaging optical system and a photographing method of the second front imaging optical system are different from each other; or
    the photographing method of the first tomographic photographing optical system and the photographing method of the second tomographic photographing optical system are different from each other and the photographing method of the first front imaging optical system and the photographing method of the second front imaging optical system are different from each other.

2. The method according to claim 1, wherein
    the difference includes a displacement between the first examinee's eye image and the second examinee's eye image.

3. The method according to claim 1, wherein
    the difference includes a difference between a scale of the first examinee's eye image and a scale of the second examinee's eye image, the method further comprising changing the scale of at least one of the first examinee's eye image and the second examinee's eye image to make the scales of both images substantially the same.

4. The method according to claim 1, wherein
    the first examinee's eye image includes at least a first front image that is a front image of the examinee's eye, and
    the second examinee's eye image includes at least a second front image that is a front image of the examinee's eye.

5. The method according to claim 4, wherein
    the first examinee's eye image further includes at least a first tomographic image that is a tomographic image of the examinee's eye, and
    the second examinee's eye image further includes at least a second tomographic image that is a tomographic image of the examinee's eye, the method further comprising:
    detecting a displacement between the first front image and the second front image; and
    correcting a displacement between the first tomographic image and the second tomographic image based on information of the displacement.

6. The method according to claim 1, wherein
    the first examinee's eye image includes at least a first tomographic image that is a tomographic image of the examinee's eye, and
    the second examinee's eye image includes at least a second tomographic image that is a tomographic image of the examinee's eye.

7. The method according to claim 6, further comprising:
    analyzing the first tomographic image and the second tomographic image by image processing; and
    obtaining differential data corresponding to a difference between an analysis result of the first tomographic image and an analysis result of the second tomographic image.

8. The method according to claim 7, further comprising displaying on a monitor a differential map made based on the differential data.

9. The method according to claim 6, wherein
    the first tomographic image and the second tomographic image are tomographic images of a fundus, the method further comprising:
    analyzing the first tomographic image and the second tomographic image by image processing, to obtain layer thickness information of the fundus based on the first tomographic image and layer thickness information of the fundus based on the second tomographic image; and
    obtaining differential data between the layer thickness information of the fundus based on the first tomographic image and the layer thickness information of the fundus based on the second tomographic image.

10. The method according to claim 6, further comprising:
    with respect to a photographing region common between the first tomographic image and the second tomographic image, obtaining differential data between an analysis result based on the first tomographic image and an analysis result based on the second tomographic image.

11. The method according to claim 1, wherein
    an optical system of the first ophthalmologic photographing apparatus for obtaining the first examinee's eye image and an optical system of the second ophthalmologic photographing apparatus for obtaining the second examinee's eye image have different structures from each other.

12. A monitoring system for carrying out the method for monitoring an image of an examinee's eye according to claim 1, comprising:
- an image processing unit configured to obtain the first examinee's eye image and additional information for determining whether the first examinee's eye image is a tomographic image or a front image, and the second examinee's eye image and additional information for determining whether the second examinee's eye image is a tomographic image or a front image; determine whether the first examinee's eye image and the second examinee's eye image are a tomographic image or a front image based on the additional information; when the first examinee's eye image and the second examinee's eye image are a tomographic image or the first examinee's eye image and the second examinee's eye image are a front image, correct a difference between the first examinee's eye image and the second examinee's eye image; and compare the first examinee's eye image with the second examinee's eye image after the difference is corrected, wherein
- the first examinee's eye image is captured on a day that is different from a day on which the second examinee's eye image is captured.

13. The method according to claim 1, wherein
the correcting the difference between the first examinee's eye image and the second examinee's eye image comprises adjusting a scale of the first examinee's eye image to match a scale of the second examinee's eye image.

14. The monitoring system according to claim 12, wherein
the image processing unit is further configured to adjust a scale of the first examinee's eye image to match a scale of the second examinee's eye image.

15. The method according to claim 1, wherein
the first front imaging optical system is one of a scanning laser ophthalmoscope, an optical coherence tomography front image photographing optical system, and a fundus camera optical system,
the second front imaging optical system is one of a scanning laser ophthalmoscope, an optical coherence tomography front image photographing optical system, and a fundus camera optical system, and the second front imaging optical system is other than the one that the first front imaging optical system is, and
the photographing method of the first front imaging optical system and the photographing method of the second front imaging optical system are different from each other.

16. The method according to claim 1, wherein
the first tomographic photographing optical system is one of a spectrum domain optical coherence tomography apparatus, a swept-source optical coherence tomography apparatus, and a time-domain optical coherence tomography apparatus, and
the second tomographic photographing optical system is one of a spectrum domain optical coherence tomography apparatus, a swept-source optical coherence tomography apparatus, and a time-domain optical coherence tomography apparatus, and the second tomographic photographing optical system is other than the one that the first tomographic photographing optical system is.

17. The method according to claim 1, further comprising:
- detecting a displacement between the front image of the first examinee's eye image and the front image of the second examinee's eye image;
- determining layer thickness information of the tomographic image of the first examinee's eye image and layer thickness information of the tomographic image of the second examinee's eye image based on the detected displacement; and
- obtaining differential data between the layer thickness information of the tomographic image of the first examinee's eye image and the layer thickness information of the tomographic image of the second examinee's eye image.

18. The method according to claim 1, further comprising:
obtaining differential data based on an comparison result of the first examinee's eye image with the second examinee's eye image.

* * * * *